United States Patent
Ferres et al.

(10) Patent No.: US 7,462,849 B2
(45) Date of Patent: Dec. 9, 2008

(54) STERILIZING LAMP

(75) Inventors: Martin Ferres, Solingen (DE); Martin Kirsten, Burscheid (DE)

(73) Assignee: Baro GmbH & Co. KG, Leichlingen (DE)

( * ) Notice: Subject to any disclaimer, the term of this patent is extended or adjusted under 35 U.S.C. 154(b) by 121 days.

(21) Appl. No.: 11/270,470

(22) Filed: Nov. 10, 2005

(65) Prior Publication Data
US 2006/0113485 A1 Jun. 1, 2006

(30) Foreign Application Priority Data
Nov. 26, 2004 (EP) .................. 04028174

(51) Int. Cl.
*A61N 5/06* (2006.01)
(52) U.S. Cl. .............. 250/504 R; 250/493.1; 250/503.1; 250/504 H
(58) Field of Classification Search .......... 250/461.1, 250/493.1–504 H
See application file for complete search history.

(56) References Cited
U.S. PATENT DOCUMENTS

| | | |
|---|---|---|
| 4,048,537 A | 9/1977 | Blaisdell |
| 5,208,816 A | 5/1993 | Seshardi et al. |
| 5,625,814 A | 4/1997 | Luciw |
| 5,748,974 A | 5/1998 | Johnson |
| 6,118,939 A | 9/2000 | Nack et al. |
| 6,212,494 B1 | 4/2001 | Boguraev |
| 6,278,996 B1 | 8/2001 | Richardson et al. |
| 6,690,390 B1 | 2/2004 | Walters et al. |
| 6,901,399 B1 | 5/2005 | Corston et al. |
| 6,904,402 B1 | 6/2005 | Wang et al. |
| 2002/0026188 A1* | 2/2002 | Balbierz et al. .......... 606/41 |
| 2002/0042793 A1 | 4/2002 | Choi |
| 2002/0045463 A1 | 4/2002 | Chen et al. |
| 2002/0065959 A1 | 5/2002 | Kim et al. |
| 2002/0124115 A1 | 9/2002 | McLean et al. |
| 2002/0143949 A1 | 10/2002 | Rajarajan et al. |
| 2002/0152190 A1 | 10/2002 | Biebsheimer et al. |
| 2003/0084035 A1 | 5/2003 | Emerick |

(Continued)

FOREIGN PATENT DOCUMENTS

DE 972 572 8/1959

(Continued)

OTHER PUBLICATIONS

U.S. Appl. No. 11/290,076, filed Nov. 30, 2005, Ramsey, et al.

(Continued)

*Primary Examiner*—Jack I. Berman
*Assistant Examiner*—Andrew Smyth
(74) *Attorney, Agent, or Firm*—Berenato, White & Stavish

(57) ABSTRACT

The invention relates to a UV-C sterilizing lamp for the treatment of a medium with UV-C radiation in order to kill the microorganisms contained therein by means of at least one UV-C emitter (2). The emitter has an elongated emitter foundation (3) and at least one electrical connection (4), and a base (5) holding the UV-C emitter (2). The at least the emitter foundation (3) of the UV-C emitter (2) is surrounded by a flexible protective cover (6), which is radiolucent to UV-C radiation.

The invention furthermore relates to a sterilizing system with at least one UV-C sterilizing lamp of the invention.

13 Claims, 2 Drawing Sheets

U.S. PATENT DOCUMENTS

| | | | |
|---|---|---|---|
| 2003/0120700 A1 | 6/2003 | Boudnik et al. | |
| 2003/0138346 A1* | 7/2003 | Gunn et al. | 422/24 |
| 2003/0214256 A1 | 11/2003 | Baarman | |
| 2004/0030556 A1 | 2/2004 | Bennett | |
| 2004/0030710 A1 | 2/2004 | Shadle | |
| 2004/0034652 A1 | 2/2004 | Hofmann et al. | |
| 2004/0111419 A1 | 6/2004 | Cook et al. | |
| 2004/0117395 A1 | 6/2004 | Gong et al. | |
| 2004/0130572 A1 | 7/2004 | Bala | |
| 2004/0250255 A1 | 12/2004 | Kraiss et al. | |
| 2005/0028133 A1 | 2/2005 | Ananth et al. | |
| 2005/0034098 A1 | 2/2005 | DeSchryver et al. | |
| 2005/0049852 A1 | 3/2005 | Chao | |
| 2005/0049874 A1 | 3/2005 | Coffman et al. | |
| 2005/0065995 A1 | 3/2005 | Milstein et al. | |
| 2005/0075859 A1 | 4/2005 | Ramsey | |
| 2005/0075878 A1 | 4/2005 | Balchandran et al. | |
| 2005/0078805 A1 | 4/2005 | Mills et al. | |
| 2005/0080625 A1 | 4/2005 | Bennett et al. | |
| 2005/0080782 A1 | 4/2005 | Ratnaparkhi et al. | |
| 2005/0114854 A1 | 5/2005 | Padisetty et al. | |
| 2005/0131672 A1 | 6/2005 | Dalal et al. | |
| 2005/0132380 A1 | 6/2005 | Chow | |
| 2006/0167531 A1* | 7/2006 | Gertner et al. | 607/86 |

FOREIGN PATENT DOCUMENTS

| | | |
|---|---|---|
| WO | WO 02/089859 A1 | 11/2002 |
| WO | WO 2004/017230 A1 | 2/2004 |
| WO | WO 2005/036365 A2 | 4/2005 |

OTHER PUBLICATIONS

U.S. Appl. No. 11/246,847, filed Oct. 7, 2005, Ramsey, et al.

U.S. Appl. No. 11/270,393, filed Nov. 9, 2005, Ramsey, et al.

U.S. Appl. No. 11/294,581, filed Dec. 5, 2005, Yao, et al.

U.S. Appl. No. 11/294,262, filed Dec. 5, 2005, Ramsey, et al.

U.S. Appl. No. 11/294,265, filed Dec. 5, 2005, Ramsey, et al.

"DTS: Programming: Creating the Custom Task Framework", 1 page, accessible at: http://msdn.microsoft.com/library/default.asp?url=/library/en-us/dtsprog/dtspcusttskc__3hwr.asp, last accessed Jan. 5, 2006.

Ernst, et al., "A Task Framework for the Web Interface W2H", Bioinformatics, 2003, pp. 278-282, vol. 19, No. 2, Oxford University Press.

Multi-Agent Systems Lab, "TAEMS: A Framework for Task Analysis, Environment Modeling, and Simulation", 3 pages, accessible at: http://dis.cs.umass.edu/research/taems/, last accessed Jan. 5, 2006.

Hochberg, et al., "A Flexible Framework for Developing Mixed-Initiative Dialog Systems", Association for Computational Linguistics, Proceedings of the Third SIGdial Workshop on Discourse and Dialogue, Jul. 2002, pp. 60-63, Philadelphia.

AgileTek, "Componentized Architecture", 2 pages, accessible at: http://www.agiletek.com/agileplus#CompArchitecture, last accessed Jan. 5, 2006.

H. Lieberman, et al., "Instructible Agents: Software That Just Keeps Getting Better", IBM Systems Journal, 1996, pp. 539-556, vol. 35, Nos. 3 and 4.

"Technical Forum: Machine Intelligence and the Turing Test", IBM Systems Journal, 2002, pp. 524-539, vol. 41, No. 3.

O. Conlan, et al., "Applying Adaptive Hypermedia Techniques to Semantic Web Service Composition", In Proceedings of AH 2003: Workshop on Adaptive Hypermedia and Adaptive Web-based Systems, 2003, pp. 53-62.

H. Liu, et al., "GOOSE: A Goal-Oriented Search Engine with Commonsense", Adaptive Hypermedia and Adaptive Web-Based Systems, Second International Conference, AH 2002, Malaga, Spain, May 29-31, 2002, Lecture Notes in Computer Science, pp. 253-263, No. 2347.

Leon Peshkin, "Research Statement", 2 pages, accessible at: http://people.csail.mit.edu/pesha/my__res.pdf, last accessed Jan. 5, 2006.

Korns Associates "Our Intelligent Agents", 4 pages, accessible at: http://www.korns.com/technology.htm, last accessed Jan. 5, 2006.

V. Chepegin, et al., "CHIME: Service-Oriented Framework for Adaptive Web-Based Systems", in Paul De Bra (ed): Proceedings of Dutch national conference InfWet, Eindhoven, the Netherlands, Nov. 20, 2003, pp. 29-36.

Esposito, Dino. "Browser Helper Objects:The Browser the Way You Want It." Microsoft Corporation, Jan. 1999, 12 pages.

* cited by examiner

STERILIZING LAMP

CROSS-REFERENCE TO RELATED APPLICATIONS AND CLAIM TO PRIORITY

This application is based upon application number 04 028 174.3, filed Nov. 26, 2004 with the European patent Office, the disclosure of which is incorporated herein by reference and to which priority is claimed.

FIELD OF THE INVENTION

The present invention relates to a UV-C sterilizing lamp for the treatment of a medium with UV-C radiation in order to kill the therein contained microorganisms by means of at least one UV-C emitter, which has an elongated emitter foundation, and at least one electrical connection, as well as a base holding the UV-C emitter, as well as a UV-C emitter for the application in such a UV-C sterilizing lamp.

BACKGROUND OF THE INVENTION

UV-C sterilizing lamps are used for the sterilization of air in commercially and industrially used spaces as well as in hospitals and airplanes. Their germicidal UV-C line-radiation with a wavelength of $\lambda=253.75$ nm is being used to kill bacteria, fungi, or viruses, or other microorganisms.

Food production represents a further area of application, in which the UV-C germinating lamps are used for sterilizing packaging materials for food products, of operational equipment, and for the sterilization of air.

A disadvantage of the known UV-C sterilizing lamps is on the one hand, that they are sensitive to water spray and water jets. On the other hand, the emitter foundation of such a UV-C sterilizing lamp may break, so that the falling splinters of the UV-C sterilizing lamp contaminate the treated goods, or get into the cycle of air sterilizing systems, without this being noticed.

The invention is therefore based on the objective of providing an improvement to the known UV-C sterilizing lamps, which meet the strict requirements with respect to hygiene and operating safety.

SUMMARY OF THE INVENTION

This task is solved in that at least the emitter foundation of the UV-C emitter is surrounded by a flexible protective cover, which is radiolucent to UV-C radiation. Teflon for example is a material, which is radiolucent to UV-C radiation.

The provision of a flexible protective cover guarantees that in the event the emitter foundation breaks, no splinters can get unnoticed onto the treatment goods arranged underneath of the UV-C sterilizing lamp, or into the cycle of sterilizing systems and contaminate these, but remain inside the protective cover. Furthermore, the provision of the protective cover also achieves a protection against water spray and water jets, so that the UV-C sterilizing lamps may be cleaned in the traditional way in case of dirt accumulation, and that even the requirements for a rating in the IP65 system of protection are met, which means at the same time an expansion of the potential field of application of the UV-C sterilizing lamps of the invention.

The protective cover may have a thickness of 0.1 mm to 0.5 mm, preferably 0.3 mm, depending on the application.

An embodiment of the present invention provides that the UV-C emitter is cast into the base in the area of its electrical connections by means of casting material, and thereby the base is sealed off to the environment. Here, the casting material should be resistant to UV-C radiation. The base and the UV-C emitter form a unit by means of the casting material, so that the electric elements inside of the base are protected against the penetration of humidity, and furthermore an exchange of a possibly defective UV-C emitter, for example by untrained personnel, may be effectively prevented.

It is expedient to produce the base from a ceramic body, whereby it is cost economical to fill the latter especially with glass wool as a filling material.

A further embodiment of the present invention provides that in the base of the UV-C sterilizing lamp a clamp is arranged in the base of the UV-C sterilizing lamp, by means of which the UV-C emitter is secured in the base against an undesired removal or falling out when the casting material has already been removed from the base for the disassembly of a defective UV-C emitter.

The operating systems for the emitter may be arranged separately outside of the UV-C sterilizing lamp, and the UV-C emitter may be supplied with power via a connection of the external operating systems with contacts at the base of the UV-C sterilizing lamp.

As an alternative, the UV-C emitter may be realized as high-output emitter or as a conventional UV-C compact low pressure emitter with two discharge tubes.

BRIEF DESCRIPTION OF THE DRAWINGS

With respect to additional advantageous embodiments and further developments of the invention, reference is made to the dependent claims as well as the following description of an embodiment on the basis of the appended drawings, wherein:

DETAILED DESCRIPTION OF THE PREFERRED EMBODIMENT(S)

Figure 1:
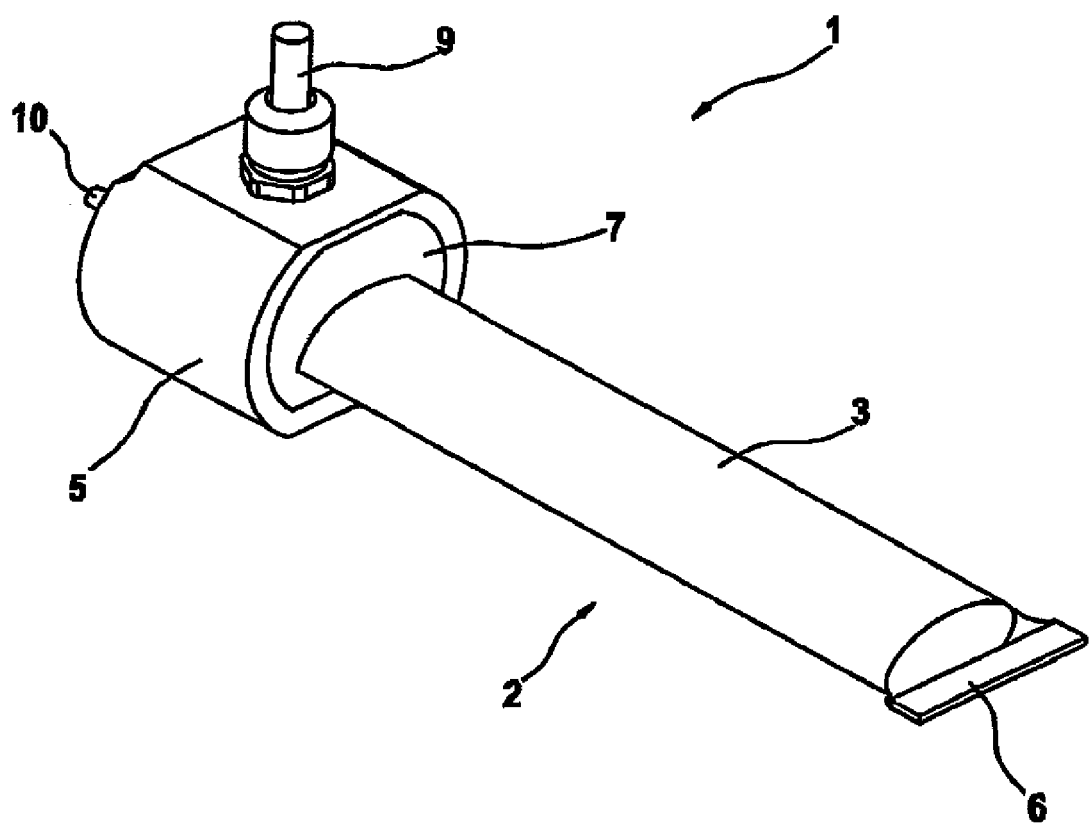
FIG. 1 Is a perspective view of the UV-C sterilizing lamp of the invention.
Figure 2:
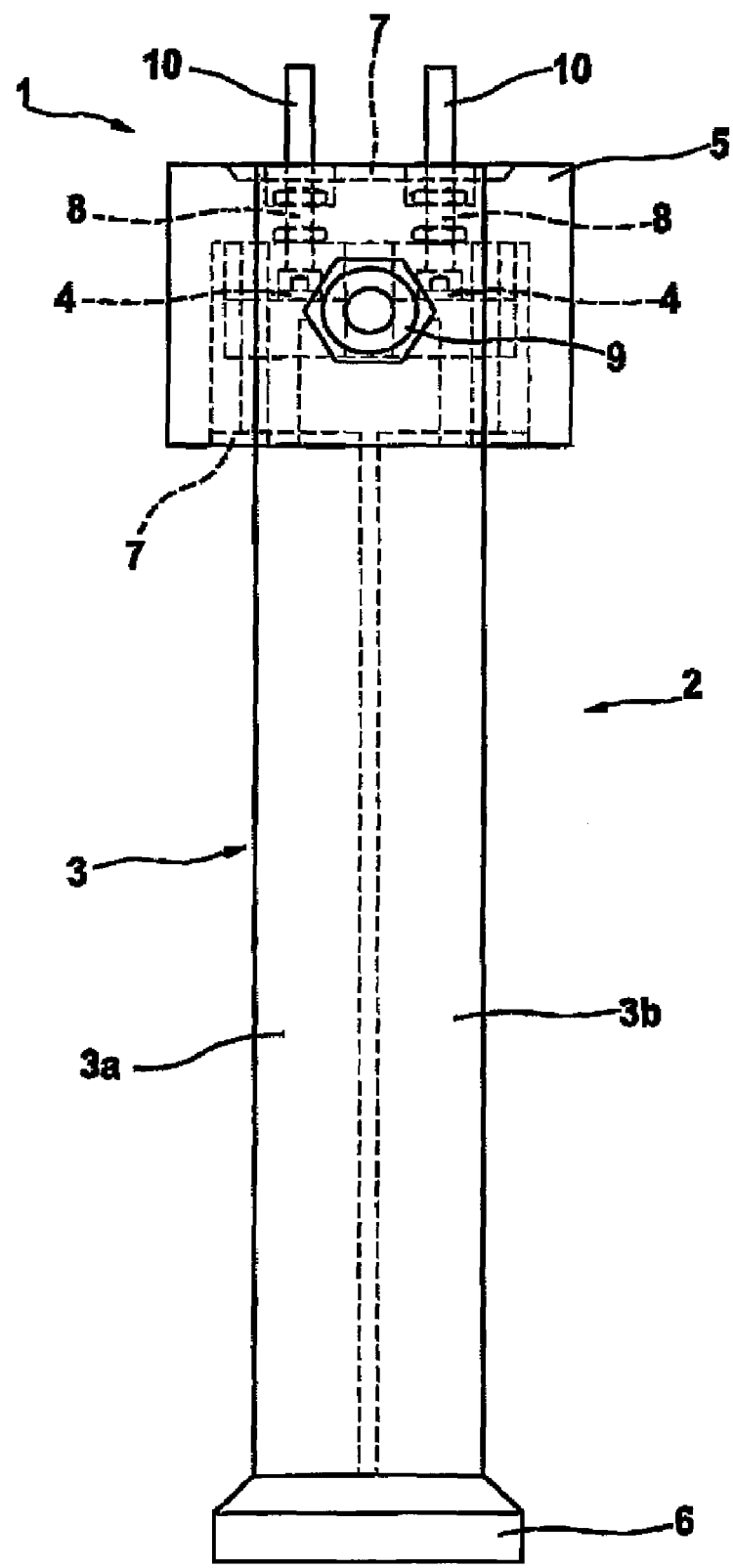
FIG. 2 Is the UV-C sterilizing lamp according to FIG. 1 from underneath.

FIGS. 1 and 2 show an embodiment of a UV-C sterilizing lamp 1 of the invention.

The UV-C sterilizing lamp 1 has a UV-C emitter 2 in the form of a high-output-UV-C compact low presser emitter. The UV-C emitter 2 has an emitter foundation 3, shown here by way of example with two discharge tubes 3a, 3b, and electrical connections 4, via which the UV-C emitter 2 is connected with the base 5. The emitter foundation 3 is completely surrounded by a flexible protective cover 6, which is radiolucent to UV-C radiation and made from Teflon with a foil thickness of about 0.3 mm.

In the area of its electrical connections 4, the UV-C emitter 2 is secured in the base via a clamp (not shown), and is cast into the base 5 by means of a UV-C radiation-resistant casting material 7, in order to protect the electrical elements arranged in the base 5 from the penetration of humidity. In this embodiment the base 5 and the UV-C emitter 2 are also connected additionally via bolted connections 8 with each other. The bolted connections are also sealed off to the environment, for example by the casting material. At the top of the base 5, a cable lead 9 is also planned.

The base 5 has contacts 10 on the side facing away from the UV-C emitter, via which the UV-C sterilizing lamp may be connected to the power supply with operating technology (not shown), which is arranged outside of the UV-C sterilizing lamp 1.

The protective cover 6 is for example welded to the end of the UV-C emitter 2 facing away from the base, so that the UV-C emitter 2 contained in the protective cover 6, is completely surrounded by the protective cover 6. Here it is sealed off against the environment and thus against humidity, especially from spray water and water jets. In a possible breakage of the emitter foundation 3, therefore, no splinters may get unnoticed onto the treated goods arranged underneath the UV-C sterilizing lamp 1, or into the cycle of sterilization systems, and contaminate them, but will remain inside of the protective cover 6. The protective cover 6 additionally functions as a heat insulation protector, so that a decrease of the radiation performance when used in cold environments is prevented.

We claim:

1. UV-C sterilizing lamp for the treatment of a medium with UV-C radiation, in order to kill the microorganisms contained therein, with at least one UV-C emitter, which has an elongated emitter foundation (3), and at least one electrical connection (4), and a base containing the UV-C emitter, characterized in that the UV-C emitter is cast into the base in the area of its electrical connections by means of casting material and at least the emitter foundation of the UV-C emitter is surrounded by a flexible protective cover, which is radiolucent to UV-C radiation.

2. The UV-C sterilizing lamp (1) according to claim 1, characterized in that the protective cover (6) is made of Teflon.

3. The UV-C sterilizing lamp (1) according to claim 1, characterized in that the protective cover has a thickness of 0.1 mm to 0.5 mm, preferably of 0.3 mm.

4. The UV-C sterilizing lamp (1) according to claim 1, characterized in that the casting material (7) is resistant to UV-C radiation.

5. The UV-C sterilizing lamp (1) according to one of the preceding claims characterized in that the base (5) is formed from a ceramics body, which is especially filled with glass wool as filling material.

6. UV-C sterilizing lamp (1) according to claim 1 characterized in that the UV-C emitter (2) is secured against involuntary removal or falling out of the base (5) by means of a clamp arranged in the base (5).

7. The UV-C sterilizing lamp (1) according to claim 1 characterized in that an operating technology for the UV-C emitter (2) is arranged separately outside of the UV-C sterilizing lamp (1).

8. The UV-C sterilizing lamp (1) according to claim 1 characterized in that the UV-C emitter (2) is a compact emitter.

9. The UV-C sterilizing lamp (1) according to claim 1 characterized in that the UV-C emitter (2) is a high output emitter.

10. The UV-C sterilizing lamp (1) according to claim 1 characterized in that the UV-C emitter (1) is a high output UV-C compact low pressure emitter with two discharge tubes (3a, 3b).

11. A UV-C emitter with an elongated emitter foundation and at least one electrical connection, characterized in that the UV-C emitter is cast into a base in the area of the at least one electrical connection by means of casting material and is surrounded by a flexible protective cover, which is radiolucent to UV-C radiation, particularly made from Teflon, at least in the area of the emitter foundation.

12. The UV-C emitter according to claim 11 characterized in that the protective cover has a thickness of 0.1 mm to 0.5 mm, preferably 0.3 mm.

13. A sterilizing facility with at least one UV-C sterilizing lamp (1) according to claim 1.

* * * * *